(12) United States Patent
Gazenko

(10) Patent No.: US 8,420,384 B2
(45) Date of Patent: Apr. 16, 2013

(54) APPARATUS FOR MAKING A SOLID NUTRIENT MEDIUM AND ASSOCIATED METHOD

(75) Inventor: Sergey V. Gazenko, Cincinnati, OH (US)

(73) Assignee: Nanologix, Inc., Hubbard, OH (US)

( * ) Notice: Subject to any disclaimer, the term of this patent is extended or adjusted under 35 U.S.C. 154(b) by 376 days.

(21) Appl. No.: 11/850,774

(22) Filed: Sep. 6, 2007

(65) Prior Publication Data

US 2008/0057562 A1    Mar. 6, 2008

Related U.S. Application Data

(60) Provisional application No. 60/824,677, filed on Sep. 6, 2006.

(51) Int. Cl.
*C12M 1/22* (2006.01)
(52) U.S. Cl.
USPC ..................... 435/305.4; 435/305.1
(58) Field of Classification Search ............... 435/305.4, 435/305.1
See application file for complete search history.

(56) References Cited

U.S. PATENT DOCUMENTS

| 2,144,255 | A | * | 1/1939 | Carpenter | 435/305.1 |
| 3,769,936 | A | * | 11/1973 | Swanson et al. | 119/6.5 |
| 3,791,930 | A | * | 2/1974 | Saxholm | 435/33 |
| 5,348,885 | A | * | 9/1994 | Labarthe | 435/305.4 |
| 6,156,566 | A | * | 12/2000 | Bryant | 435/305.3 |
| 6,472,203 | B1 | * | 10/2002 | Gallup et al. | 435/309.1 |

* cited by examiner

*Primary Examiner* — Michael Marcheschi
*Assistant Examiner* — Jonathan Hurst
(74) *Attorney, Agent, or Firm* — Acker Wood IP Law, LLC; Gwen R. Acker Wood

(57) ABSTRACT

The present invention provides an apparatus comprised of devices for simple, fast and cost-effective storage and plating of solid nutrient medium (SNM) for various uses in the field of microbiological analysis. The devices consist of a container which can be aseptically filled with SNM and equipped with a plunger to accurately press out needed amounts of the SNM; a cutting means to cut, hold and transfer SNM; a measuring means to measure the amount of SNM exiting the container; and a growth plate for storage of SNM, growth of microorganisms on SNM, and introduction of indicator substances to SNM for analysis of microorganisms.

10 Claims, 5 Drawing Sheets

US 8,420,384 B2

APPARATUS FOR MAKING A SOLID NUTRIENT MEDIUM AND ASSOCIATED METHOD

The present application claims priority to U.S. Provisional Application No. 60/824,677, filed Sep. 6, 2006, which is incorporated herein by reference.

BACKGROUND OF THE INVENTION

1. Field of the Invention

The present invention relates generally to solid nutrient media (SNM). More particularly, the present invention relates to an apparatus comprised of devices for making and plating a solid nutrient medium and methods thereof.

2. Background Information

Solid nutrient media (SNM) have various uses in microbiology, health care, the food industry, biotechnology, ecology and research. Microorganisms can proliferate on the surface of media ("direct method") or inside media ("pour method"). The majority of microorganisms, such as bacteria, actinomycetes, fungi, and yeasts, i.e., hundreds of thousands of different species, are able to grow on nutrient agars. Nutrient agars are vital to the operation of microbiological laboratories. These laboratories rely on SNM for the growth of microorganisms which can exist in an investigated sample, for maintenance of microorganism collections for research purposes or quality control, for environmental control of indoor and outdoor air and for wash-outs from surfaces such as instruments, equipment, work surfaces and walls.

Samples containing microorganisms can be deposited on SNM by direct transfer of a liquid or solid sample on the surface of the SNM, by transfer filter with cells after filtration, or by impression of SNM onto an investigated surface.

Billions of growth plates ("Petri plates") are used worldwide for different microbiological purposes, and well over 80-90% of currently used methods are based on preliminary growth of microorganisms, typically on solid media. For example, in 1999, the United States food industry conducted 144 million quality control tests, in which over 100 million of these tests required the use of nutrient agars (T. R. Weschler, American Clinical Laboratory, April 2001). This number does not include the millions of growth plates used in medical, veterinarian, biochemical, pharmaceutical, environmental, agricultural, research and educational microbiological laboratories. Thus, the total amount of growth plates used annually in the United States alone is in the hundreds of millions.

Petri/growth plates, therefore, are a vital part of microbiological analytical procedures, but they also are a substantial portion of a laboratory's expenses.

Since its introduction in 1877, growth plates, also referred to as Petri plates or Petri dishes, have remained largely unchanged. The typical Petri plate is a shallow cylindrical plate with a lid, in which air is allowed to enter the plate for aeration by passing through a slot between the lid and the plate. Much effort by microbiologists in the last century has been focused on the improvement of existing nutrient media and creating different nutrient media for the growth of different kinds of microorganisms. Numerous varieties of media have been created, the majority of which are in a solid phase with an agar base. Petri plates, however, have undergone far less changes over the years. For example, glass Petri plates have been replaced with plastic (i.e., polystyrene, polycarbonate) disposable plates, which have eliminated the costly and time-consuming process of cleaning and autoclaving. Several different shapes of Petri dishes (such as rectangular) and sizes have appeared on the market. Some plates currently are being manufactured with multiple inner compartments, which allows for the use of different media or additives in the same plate. For example, Nunclon® multidishes (Nunc, Inc.) are manufactured with 4 to 48 wells (cylindrical and rectangular) under one lid. These plates have found use in various fields, such as cytology and virology.

There exists a need, therefore, to provide a simpler, more efficient, cost-effective apparatus for manufacturing and plating of solid nutrient medium.

SUMMARY OF THE INVENTION

The present invention meets this need by providing an apparatus comprised of several devices and associated methods for manufacturing and plating of a solid nutrient medium (SNM).

In an aspect of the present invention, there is provided a storage device for preparing solid nutrient medium, the storage device comprising a container having a channel extending therethrough, an outer surface, a first end and a second end, wherein the channel is structured to receive melted nutrient medium which is allowed to solidify; the container also having a plunger located adjacent to the second end of the container and adapted to travel through the channel of the container when a force is applied to the plunger, wherein when the plunger travels through the channel, the plunger is structured to push the solidified nutrient medium through the first end of the container; and a measuring means positioned on the outer surface of the container for measuring the thickness of the solidified nutrient medium that exits the first end of the container.

In another aspect of the present invention, there is provided a growth plate, comprising a growth plate lid having an exterior surface, an interior surface and a perimeter, the growth plate lid comprising an outer lid ring having an interior surface with at least one indentation therein, the outer lid ring extending substantially perpendicular from the interior surface of the growth plate lid, the outer lid ring being disposed substantially adjacent to the perimeter of the growth plate lid; and an inner lid ring having an interior surface and at least one slot therein, the inner lid ring extending substantially perpendicular from the interior surface of the growth plate lid; and a growth plate dish having an exterior surface, an interior surface and a perimeter, the growth plate dish comprising an outer dish ring having at least one slot therein, the outer dish ring extending substantially perpendicular from the interior surface of the growth plate dish; a middle dish ring having at least one slot therein, the middle dish ring extending substantially perpendicular from the interior surface of the growth plate dish; and an inner dish ring having a plurality of spaced members, the members extending substantially perpendicular from the interior surface of the growth plate dish, wherein the outer dish ring is positioned substantially adjacent to the interior surface of the outer lid ring, and the middle dish ring is positioned substantially adjacent to the interior surface of the inner lid ring.

In another aspect of the present invention, there is provided a method for preparing a solid nutrient medium, comprising providing the container described hereinabove; providing a melted nutrient medium; pouring the melted nutrient medium into the channel of the container; allowing the melted nutrient medium to solidify; applying a force to the plunger of the container so that the plunger begins to travel from the second end towards the first end of the container in order to push the solidified nutrient medium through the first end of the container; and providing a cutting means for cutting the solidified nutrient medium after it has extended beyond the first end of the container. The method further comprises cutting the solidified nutrient with the cutting means and transferring the cut slice of the solidified nutrient medium with the cutting means onto a growth plate.

BRIEF DESCRIPTION OF THE DRAWINGS

A full understanding of the invention can be gained from the following description of the preferred embodiments when read in conjunction with the accompanying drawings in which:

FIG. 1A shows the container in a closed condition and FIG. 1B shows the various parts of the container;

FIG. 4A is a top view of the lid; FIG. 4B is an elevation view of the lid; and FIG. 4C is a cross-sectional view of the lid;

FIG. 5A is a top view of the plate; FIG. 5B is an elevation view of the plate; and FIG. 5C is a cross-sectional view of the plate.

DESCRIPTION OF THE PREFERRED EMBODIMENTS

Figure 1:
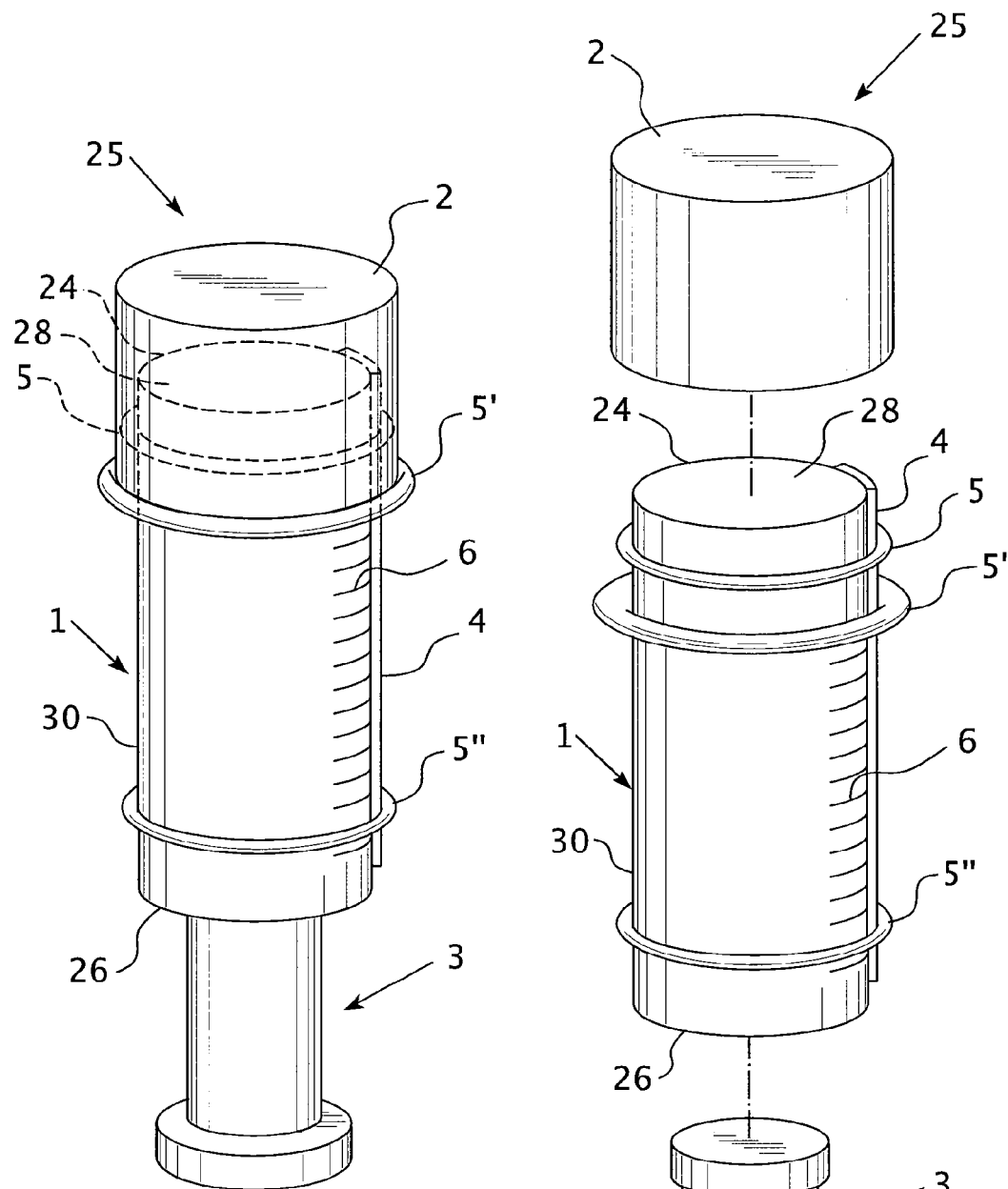
FIGS. 1 A, B show an elevation view of a container for storage of solid nutrient media (SNM) in accordance with embodiments of the invention.

The present invention provides an apparatus comprised of several devices and associated methods for manufacturing and plating a solid nutrient medium (SNM).

When referring to any numerical range of values, such ranges are understood to include each and every number and/or fraction between the stated range minimum and maximum.

Directional phrases used herein, such as, for example, upper, lower, left, right, vertical, horizontal, top, bottom, above, beneath, clockwise, counterclockwise and derivatives thereof, relate to the orientation of the elements shown in the drawings and are not limiting upon the claims unless expressly recited therein.

The present invention is directed to the manipulation of solid nutrient media (SNM). As used herein, the terms "solid nutrient media," "solid nutrient medium," "nutrient medium" and "nutrient agar" are interchangeable and refer to any nutrient medium having a gel base.

As used herein, the term "agar" means pure agar which can be used by itself or as a substance filled with dyes or artificial substrates.

As used herein, the term "artificial substrate" refers to substances transformed by enzymes in colored or fluorescent substances. Artificial substrates can be "chromogenic," i.e., producing color substances, or "fluorogenic," i.e., producing fluorescent substances.

As used herein, the terms "growth plate," "Petri plate" and "Petri dish" all are interchangeable.

The current invention can be used for different purposes in microbiological laboratories, such as for example and without limitation, for microbiological research, for control of contamination; for environmental control of surfaces, air, and equipment; and for maintaining microorganism collections in microbiological laboratories. Therefore, several different embodiments are possible with the use of the devices of the apparatus of the present invention, i.e., they can be used together in a set or used separately.

A complete understanding of the present invention will be obtained from the following description taken in connection with the accompanying drawing figures, wherein like reference characters identify like parts throughout.

In an embodiment of the present invention, there is provided an apparatus comprised of three devices. Specifically, as shown in FIGS. 1A, B, one device of the apparatus of the present invention is a storage container 25 for storing and preparing solid nutrient medium. FIG. 1A shows an assembled storage container 25 and FIG. 1B shows the various parts of the storage container 25. The storage container 25 consists of a container 1, such as a cylinder, having a channel 28 extending therethrough, an outer surface 30, a first end 24 and a second end 26, wherein the channel 28 is structured to receive melted nutrient medium which is allowed to solidify; a container lid 2; a plunger 3 located adjacent to the second end 26 of the container 1 and being adapted to travel through the channel 28 of the container 1 when a force is applied to the plunger 3, wherein when the plunger 3 travels through the channel 28, the plunger 3 is structured to push solidified nutrient medium through the first end 24 of the container 1; and a measuring means 4, 6 positioned on the outer surface 30 of the container 1 for measuring the thickness of the solidified nutrient medium that exits the first end 24 of the container 1.

The container 1 can be fabricated, for example, out of plastic or glass. The container lid 2 can be fabricated, for example, out of metal, to allow for easy sterilization by flaming.

The measuring means 4, 6 is comprised of a metal strip 4 held in position on the outer surface 30 of the container 1 by a plurality of rubber rings that easily can be removed from the outer surface 30 of the container 1; and a ruler 6 on the outer surface 30 of the container 1 for determining the position of the metal strip 4 in order to determine the thickness of the solidified nutrient medium which exits the first end 24 of the container 1. Preferably, three rings 5, 5', 5" are used, in which the two upper rings 5, 5' serve to prevent the container, lid 2 from coming into contact with the first end 24 of the container 1, thus protecting nutrient agar contained in the channel 28 of the container from contamination. One ring 5 maintains the container lid 2 in a vertical position and the other ring 5', having a slightly wider diameter, protects the container lid 2 from falling on the first end 24 of the container 1. The third ring 5" assists the other two rings 5, 5 in holding the metal strip 4 in position on the outer surface 30 of the container 1.

Figure 2:
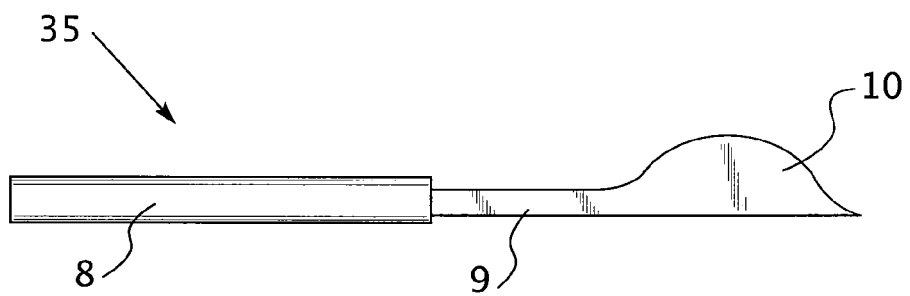
FIG. 2 shows a plan view of a cutting means for cutting the solid nutrient media from the storage container and for transferring the solid nutrient media to a growth plate in accordance with embodiments of the invention.

As shown in FIG. 2, a second device of the apparatus of the present invention is a cutting means 35 for cutting the solidified nutrient medium after the solidified nutrient medium has extended beyond the first end 24 of the container 1. The cutting means 35 preferably is a knife comprised of a handle 8 and a blade 9, in which the blade 9 expands outwardly at the end of the blade 9 furthest from the handle 8 to form a ledge 10, the ledge 10 structured to hold on its surface and to transport the solidified nutrient medium after being cut by the blade 9.

Figure 3:
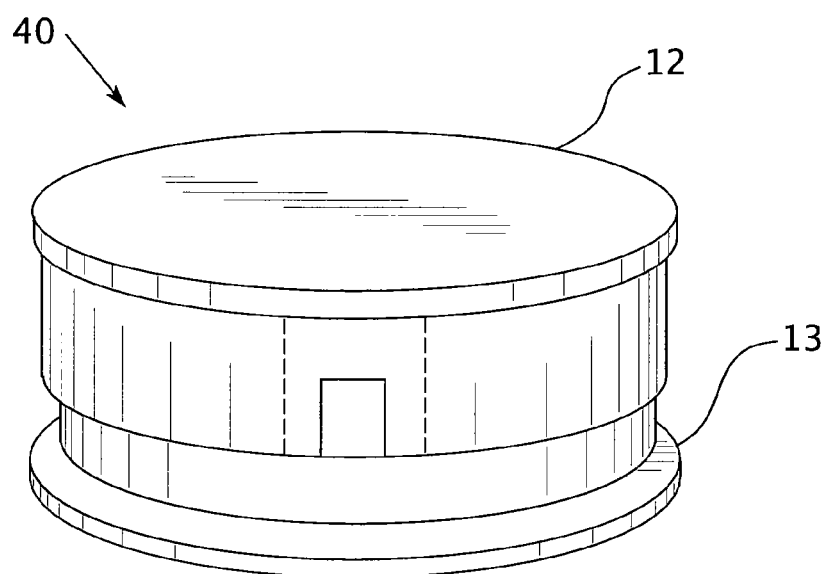
FIG. 3 shows an elevation view of the growth plate in accordance with embodiments of the invention.

As shown in FIG. 3, a third device of the apparatus of the present invention is comprised of a growth plate 40 having a growth plate lid 12 and a growth plate dish 13.

Figure 4A:
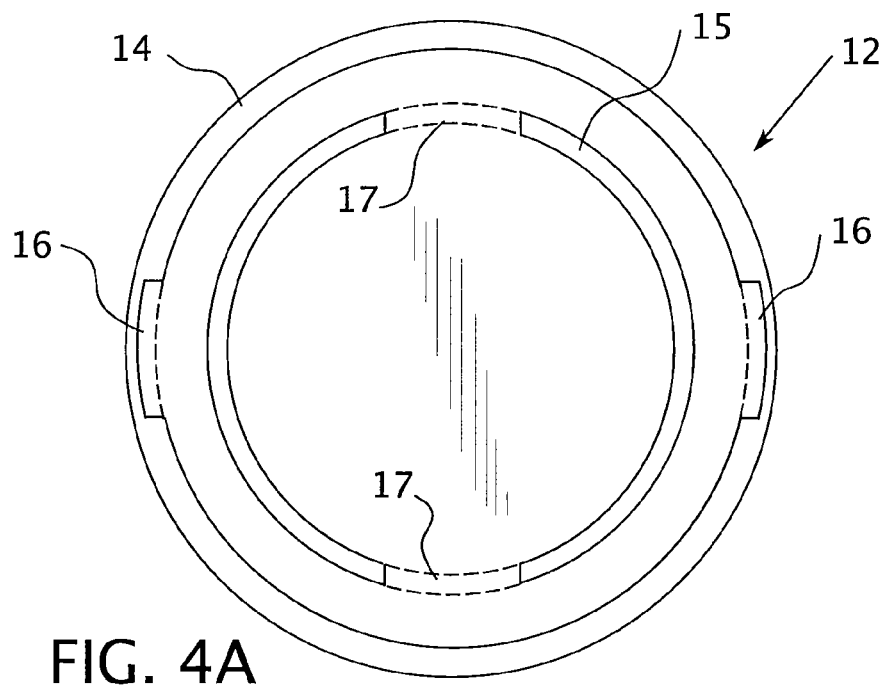
FIGS. 4A-C show three positions of a growth plate lid in accordance with embodiments of the invention.

As shown in FIGS. 4A, B, the growth plate lid 12, having an exterior surface, an interior surface and a perimeter, is comprised of an outer lid ring 14 having an interior surface with at least one indentation 16 therein, the outer lid ring 14 extending substantially perpendicular from the interior surface of the growth plate lid 12, the outer lid ring 14 being disposed substantially adjacent to the perimeter of the growth plate lid 12; and an inner lid ring 15 having an interior surface and at least one slot 17 therein, the inner lid ring 15 extending substantially perpendicular from the interior surface of the growth plate lid 12.

The inner lid ring 15 can be substantially circular in shape. The outer lid ring 14 can be substantially circular or rectangular (not shown) in shape.

Figure 5A:
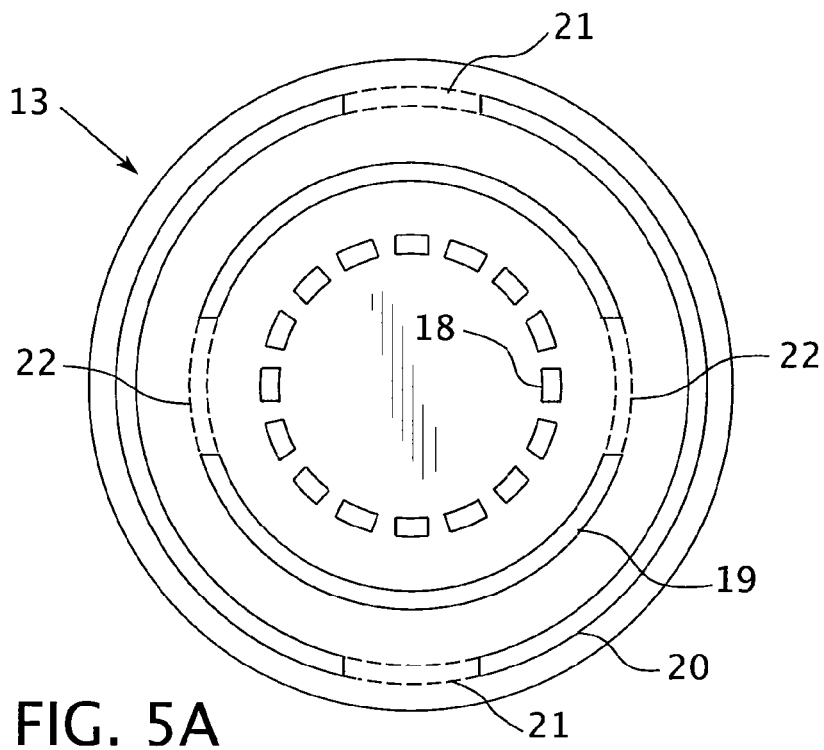
FIGS. 5A-C show three positions of a growth plate dish in accordance with embodiments of the invention.

As shown in FIGS. 5A, B, the growth plate dish 13, having an exterior surface, an interior surface and a perimeter, is comprised of an outer dish ring 20 having at least one slot 21 therein, the outer dish ring 20 extending substantially perpendicular from the interior surface of the growth plate dish 13; a middle dish ring 19 having at least one slot 22 therein, the middle dish ring 19 extending substantially perpendicular from the interior surface of the growth plate dish 13; and an inner dish ring 18 comprised of a plurality of spaced members, the members extending substantially perpendicular from the interior surface of the growth plate dish 13, wherein the outer dish ring 20 can be positioned substantially adjacent to the interior surface of the outer lid ring 14, and the middle dish ring 19 can be positioned substantially adjacent to the interior surface of the inner lid ring 15.

The middle dish ring 19 and the inner dish ring 18 can be substantially circular in shape. The outer dish ring 20 can be substantially circular or rectangular (not shown) in shape.

All three glass dish rings 18, 19, 20 are fixed to the bottom of the growth plate dish 13. Nutrient agar sliced from the storage device 25 shown in FIG. 1 is placed in the middle of the inner dish ring 18. Once the nutrient agar slice is placed in the inner dish ring 18, there is no extra space in one embodiment between the nutrient agar slice and the inner walls of the inner dish ring 18. Thus, the diameter of the nutrient agar and the inner dish ring 18 are the approximately the same. Preferably, the inner dish ring 18 is designed with spaces (i.e., a plurality of spaced members such as segments that can be removed) for two purposes: first, to facilitate dye, substrates, antibiotics and the like that can be poured in the space between the middle dish ring 19 and the inner dish ring 18 to be freely absorbed by nutrient agar through the removable segments of the inner dish ring 18; and second, to prevent bubbles from forming under the nutrient agar, as excess air is allowed to exit through the removable segments of the inner dish ring 18. The slots 17, 21, 22 of the growth plate dish rings 18, 19, 20 also allow for aeration and its regulation.

Figure 4B:
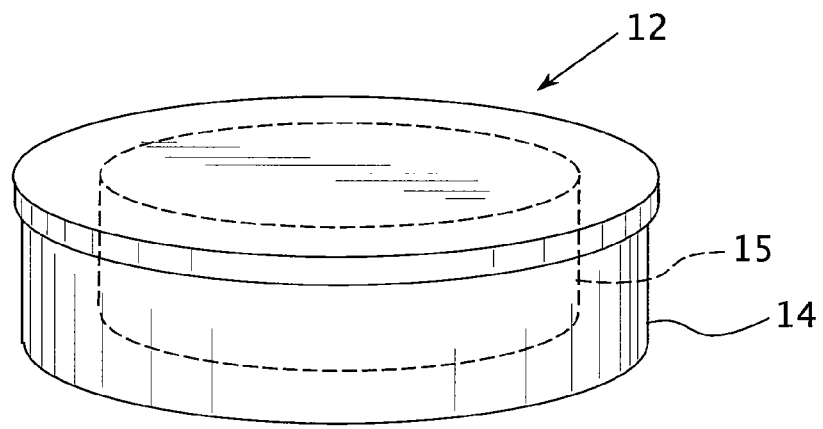
Figure 4C:
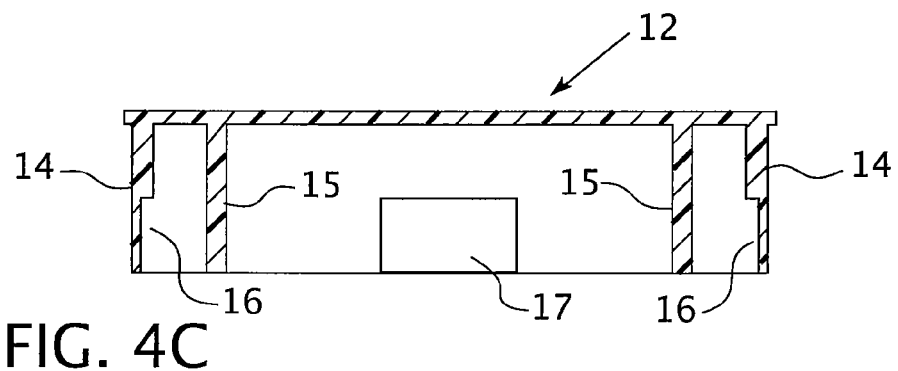

As shown in FIG. 4C, at least one indentation 16 in the outer lid ring 14 can be positioned at an angle from at least one slot 17 in the inner lid ring 15. As shown in FIG. 5C, at least one slot 21 in the outer dish ring 20 can be positioned at an angle from at least one slot 22 in the middle dish ring 19.

Figure 6A:
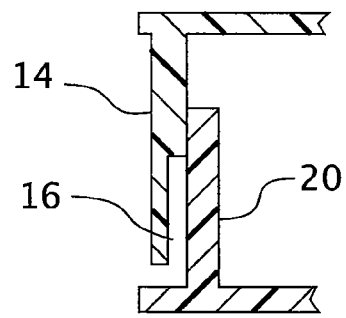
FIGS. 6A-D show the place of junction of outer rings of the growth plate lid and the growth plate dish in closed (FIG. 6A) or open (FIG. 6B) positions for aeration, and the place of junction of inner rings of the growth plate lid and the growth plate dish in closed (FIG. 6C) or open (FIG. 6D) positions for aeration.

As shown in FIGS. 4C and 6A, when the growth plate 40 is in a closed position, the at least one indentation 16 of the outer lid ring 14 of the growth plate lid 12 overlaps with the outer dish ring 20 of said growth plate dish 13 because the at least one slot 21 of the outer dish ring 20 is not adjacent to the at least one indentation 16 in the outer lid ring 14.

Figure 6B:
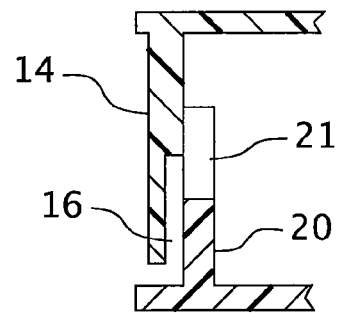

As shown in FIGS. 4C and 6B, when the growth plate 13 is in an open position, the at least one indentation 16 of the outer lid ring 14 of the growth plate lid 12 is adjacent to the at least one slot 21 in the outer dish ring 20, which opens up a passage of air in the growth plate 40, wherein said passage of air can be regulated by shifting, or rotating, the outer lid ring 14 in relation to the outer dish ring 20.

Figure 5B:
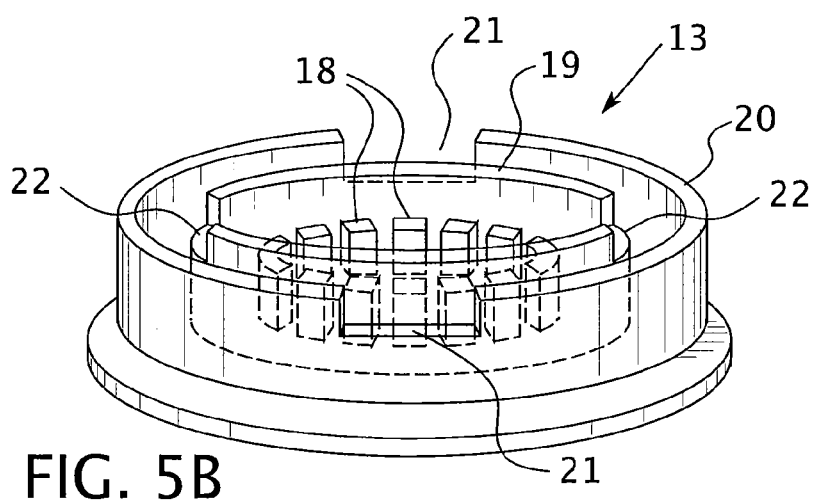
Figure 5C:
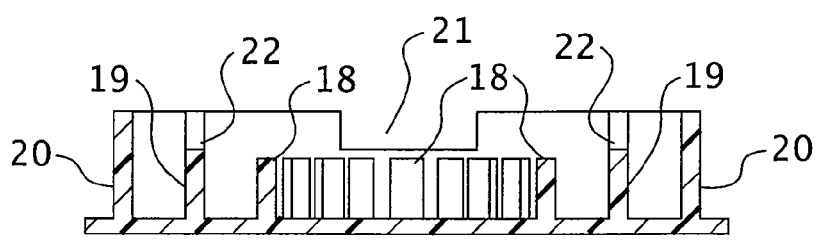
Figure 6C:
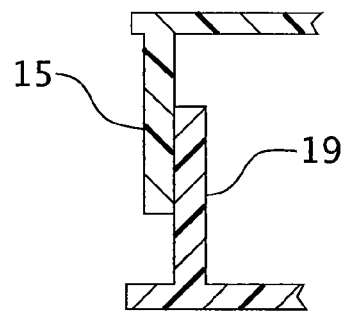
Figure 6D:
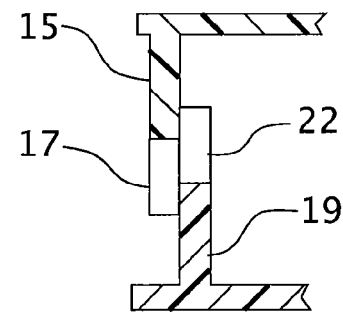

As shown in FIGS. 5C and 6D, when the at least one slot 17 of the inner lid ring 15 and the at least one slot 22 of the middle dish ring 19 are adjacent to one another, an inner passage of air is opened in the growth plate dish 13.

As shown in FIGS. 5C and 6C, when the at least one slot 17 of the inner lid ring 15 and the at least one slot 22 of the middle dish ring 19 are not adjacent to one another, inner space of the growth plate dish 13 is closed to an inner passage of air.

As shown in FIGS. 4-6, when the inner passage is closed to air, the at least one indentation 16 in the outer lid ring 14 and the at least one slot 17 of the inner lid ring 15 are positioned at an angle to the at least one slot 21 of the outer dish ring 20 and the at least one slot 22 of the middle dish ring 19, the inner space of the growth plate dish 13 being protected from contamination.

In another embodiment of the present invention, there is provided a method for preparing a solid nutrient medium, comprising providing the storage device 25 described hereinabove; providing a melted nutrient medium; pouring the melted nutrient medium into the channel 28 of the container 1 of the storage device 25; allowing the melted nutrient medium to solidify; and applying a force to the plunger 3 of the container 1 so that the plunger 3 begins to travel from the second end 26 towards the first end 24 of the container 1, the plunger 3 pushing the solidified nutrient medium through the first end 24 of the container 1.

The method further comprises providing a cutting means comprised of the knife 35 described hereinabove for cutting the solidified nutrient medium after it has extended beyond the first end 24 of the container 1.

It is contemplated and preferable to start cutting the solidified nutrient medium from the middle of the blade 9 and to finish at the ledge 10, as this prevents a piece of the solidified nutrient medium from falling down from the blade 9 and allows for a smooth cut of the solidified nutrient medium to be achieved.

The handle 8 of the knife 35 protects one's hand from heating during flaming of the blade 9. The handle 8 can be fabricated from any heat resistance material, such as, for example, wood, plastic and the like. Flaming is essential before using the knife 35 to cut nutrient agar because it protects the nutrient agar from contamination. The blade 9 can be fabricated, for example, from thin, smooth steel.

The method further comprises transferring the solidified nutrient medium onto the growth plate 40 described hereinabove after the solidified nutrient medium is cut.

The method further comprises providing the growth plate 40 as described hereinabove; transferring the solidified nutrient medium within the inner dish ring 18 of the growth plate dish 13; providing the growth plate lid 12; and covering the growth plate dish 13 with the growth plate lid 12 so that the outer dish ring 20 is positioned substantially adjacent to the interior surface of the outer lid ring 14, and the middle dish ring 19 is positioned substantially adjacent to the interior surface of the inner lid ring 15.

The method further comprises measuring the thickness of the solidified nutrient medium that exits the first end 24 of the container 1 with the measuring means 4, 6 described hereinabove.

In an embodiment, the growth and detection of microorganisms (colonies) on the surface of a filter is provided. A detailed explanation of the aforementioned described devices in light of this embodiment follows.

In order to prepare the storage device for storage or for immediate use of solid nutrient media (SNM), melted nutrient media is poured inside the container and cooled. Once the nutrient agar solidifies, it is ready for storage or for use. To store the container with the solidified nutrient agar for an extended period of time, the container is closed with the container lid that has been sterilized, and then placed in a cold room at a temperature of about 4-5° C. In the cold room, SNM can be stored according to recommendations provided with the SNM. Usually, the SNM can be stored at this temperature for several months. Storage of the SNM at room temperature is limited to about one to two months.

If nutrient agar is needed for cell cultivation, the lid of the container is removed, the strip is adjusted to a necessary level with the assistance of the ruler, the plunger pressed, and nutrient agar appears above the edge of the cylinder and a slice of the nutrient agar is cut with the knife. The slice of nutrient media then is transferred to the middle of the growth plate dish inside the inner dish ring.

In another embodiment, a sample of cells can be grown on the growth plate of the present invention and then analyzed with the use of a filter. Any suitable filter, manufactured by various companies, can be used in the present invention and are familiar to those skilled in the art. It is contemplated that the filter be the same size as the inner plate ring. A suitable filter size is, for example, 25 mm. Thus, the inner dish ring and the nutrient agar should have the same diameter. Different diameters for the filter, the inner dish ring and the nutrient agar can be used, but it is contemplated that the filter, the inner dish ring and nutrient agar all have the same diameter.

With the use of sterile forceps, the filter with a sample of cells therein can be transferred on top of the nutrient agar container. The container lid then is mounted on top of the container. Slots for aeration are adjusted for any required size and growth plate placed in the incubator. If fungi or yeast are being investigated and nutrient agar (SDA or Malt agar from BD Biosciences) is used to recover these microorganisms, the time of incubation usually needs to be extended by 3 to 5 days. Aeration needs to be maximal because fungi and yeast are strict aerobes. Because of the small size of the slice of solid nutrient medium that is provided by the present invention, which has a volume many times smaller than nutrient agar which typically is used in prior art Petri plates, the small slice of solid nutrient medium may dehydrate faster during long incubation times with open slots for aeration and at temperatures of, for example, 28-32° C. for fungi and yeast. Thus, to prevent dehydration of the nutrient agar during lengthy incubations, a small amount of distilled water, for example, about 1 to 2 ml, can be placed in the space between the middle dish ring and the outer dish ring. Evaporation of this water will produce local humidity (only inside the growth plate). This local humidity will prevent the dehydration of the small slice of nutrient agar. Because of this humidity, it is possible to replace the typically large amounts of nutrient agar used in prior art apparatuses with smaller nutrient agar slices i.e., about, for example, 10 to 30 times smaller. No prior art growth plates have a design as provided by the present invention which allows for the incorporation of local humidity in a growth plate. This effect of local humidity can be used in other ways as well, for example, for incubation at regular temperatures (i.e., 35 to 37° C.) for about 48 hours; for growth of thermophiles at about, for example 42 to 65° C.; and in conditions of low humidity in laboratories. In another example, during regular growth at about 35 to 37° C. for about 17 to 24 hours and with regular humidity in a laboratory, 50-80% local humidity is not needed. The advantage of the present invention is the ability to provide local humidity inside a growth plate so as to allow the use of a much smaller slice of nutrient agar, which is cost-effective for microbiological laboratories.

After the incubation period is over, the number of colonies can be counted. Chromogenic substrates can be added to the nutrient agar in order to color all the colonies, both large and small. For example, adding the chromogenic substrate 3-(4, 5-dimethylthiazol-2-yl)-2,5-diphenyltetrazolium bromide (MTT), which is water soluble and slightly yellow, results in a color change of dark violet in prokaryotic cells. (Many other known chromogenic substrates also can be used). The solution of MTT can be added in the space between the inner plate ring and the middle plate ring of the growth plate of the present invention. The solution of MTT will pass through the slots of the inner plate ring and dissolve in the nutrient agar in several minutes. All water soluble molecules easily can be dissolved in different nutrient agars because nutrient agars are composed of about 95 to 98% water. Also, because the present invention provides for the use of small slices of agar, this helps the chromogenic substrate to dissolve quickly. When using a chromogenic substrate and the growth plate of the present invention, all colonies, even the smallest, become well visible. Thus, the reliability and sensitivity of analysis is greatly increased. This is possible because of the space between the inner dish ring and the middle dish ring, as well as the ability to remove one or more segments of the inner dish ring to facilitate absorption of the chromogenic substrate. Adding a chromogenic substrate directly on top of the microscopic colonies, as commonly performed by those skilled in the art, is not effective because the chromogenic substrate may dissolve the majority of colonies and thus prevent accurate counting of the cells in the colonies because of attachment of the cells to one another. Adding a chromogenic substrate to nutrient agar before incubation also is ineffective, because chromogenic substrates can suppress growth of cells and colony formation in a majority of species.

For example, in trying to find a specific microorganism, such as *E. coli*, on the surface of a filter, a chromogenic substrate specific for *E. coli*, such as 5-bromo-4-chloro-3-indoxyl-β-D-glucuronic acid or sodium salt, can be used. This chromogenic substrate can be added between the inner dish ring and the middle dish ring of the growth plate of the present invention, which colors *E. coli* colonies a blue color.

In another example, in trying to determine the presence of antibiotic-resistant microorganisms, an appropriate volume and concentration of antibiotic can be added before incubation and a chromogenic substrate can be added after incubation, both additions being between the inner dish ring and the middle dish ring of the growth plate of the present invention.

As a further example, a more sensitive fluorescence method can be used, in which an appropriate fluorogenic substrate can be added after incubation between the inner dish ring and middle dish ring of the growth plate of the present invention. In this case, a black, non-fluorescent filter can be used to eliminate interference.

Any suitable nutrient medium can be used with the devices of the apparatus of the present invention. When it is necessary for the sake of analysis to use very expensive nutrient agars, it is especially advantageous to use all of the devices of the apparatus because of the ability to control how much nutrient agar is used and the ability to produce thin slices of nutrient agar.

In another embodiment, cells can be grown on the surface of nutrient agar without the use of a filter. Microbiological procedures in modern microbiological laboratories require the growth of a certain amount of cells for different purposes. In such cases it is not necessary to use the standard, more expensive large Petri plates, as the same growth of cells can be achieved with the devices of the apparatus of the present invention. Indeed, the present invention makes the use of conventional Petri plates economically practical only when a large biomass of cells is required.

In a further embodiment, cell growth in micro-channels can be used with the devices of the apparatus of the present invention. Micro-channel technology for rapid detection of microorganisms, as described in U.S. Published Patent Applications 20050221403, 20050026135 and 20030211566, all of which are incorporated herein by reference, is based on the detection and coloration (light absorption or fluorescence) of micro-colonies or single cells inside extremely small channels of a micro-channel plate mounted on a filter. In this embodiment, a filter with a micro-channel plate can be transferred on top of a nutrient agar container of the present invention and then transferred to a growth plate of the present invention. The micro-colonies which appear in about 3 to 5 hours within the micro-channels can be colored and analyzed according to well-known procedures in the art. For example, to detect a single cell trapped inside a micro-channel, a pure agar container can be used instead of a nutrient agar container. An indicator substrate then can be added to the space between the inner dish ring and the middle dish ring, which can reach the micro-channel plate by absorption through the agar to then react with the cell. The cell will produce enough fluorescence to be spotted in the micro-channel. In this example, no preliminary incubation of the microorganism is needed.

In another embodiment, the nutrient agar containers of the present invention can be used without using the growth plates of the present invention. For example, small slices of nutrient agar can be sliced using the container of the present invention and the small slices can be transferred to a regular Petri plate. This is useful when it is desired to visually compare the effects of different media on the same kind of cells, such as to investigate the influence of a substance on the growth of different species using different nutrient agars. The different nutrient agars can all be in close proximity to one another, which simplifies visual and/or microscopic analysis of the cells. In addition, the use of one conventional expensive Petri plate instead of about 10 to 20 smaller growth plates of the present invention can be more economical. Also, the use of the container of the present invention eliminates the need to use conventional methods of melting and pouring nutrient agar, adding to the efficiency and effectiveness of the analysis.

In another embodiment, the apparatus of devices of the present invention allows for combining two or more slices of nutrient agar. For example, because the inner dish ring consists of segments that are relatively low in height, and the nutrient agar sliced from the container of the present invention can be substantially higher than the segments of the inner dish ring, this provides the opportunity to cut off the top portion of the nutrient agar and transfer it for further treatment or analysis. In another example, the thicker lower slice of agar remaining after cutting off a thin slice at the top can be combined with another slice of agar cut from the container, and the thin upper slice, with cells grown on it, can be removed. These manipulations can be important in the case of fluorescent analysis of cells, in that UV light is used to produce fluorescence, but the UV light also produces background fluorescence from the nutrient media, which hinders accurate analysis. The use of a thin layer of nutrient agar produces a lot less background fluorescence than a thick layer of nutrient agar. Thus, fluorescent analysis of cells directly on agar becomes possible. No other known conventional plate affords this possibility because typically produced agars cannot be combined from two separately sliced pieces.

In another embodiment, substances can be added to nutrient agar and placed inside the inner dish ring. These substances are able to dissolve in the nutrient agar starting from the outer regions of the inner dish ring. The open channels on the bottom of the growth plate under the nutrient agar are able to increase the dissolution of the substances in the agar in a uniform manner. This is especially important when the sliced agar is relatively thick.

In another embodiment, the spaces within the growth plate of the present invention can be used for liquid samples or for creating local humidity. For example, the bottom of the growth plate has two separated spaces: (1) the space inside the middle dish ring; and (2) the space between the middle dish ring and the outer dish ring. The space inside of the middle dish ring can be used for liquid samples. The space between the middle dish ring and the outer dish ring can have water added to prevent premature drying of the liquid sample by creating local humidity.

The present invention is more particularly described in the following non-limiting examples, which are intended to be illustrative only, as numerous modifications and variations therein will be apparent to those skilled in the art.

EXAMPLES

Example 1

Analysis of Total Viable Microorganisms in Tap Water

In this investigation, 50 mL of water was filtrated through a regular filtration device with the use of a nitrocellulose filter (25 mm diameter, 0.2 μk pores, Pall Corporation). Nutrient agar (TSA, Remel, Inc.) was cut into a slice having a thickness of about 3 mm from a container of the present invention with the help of a previously flamed knife for slicing. The nutrient agar slice was transferred into the middle of a growth plate of the present invention. A filter containing sediment microorganisms was transferred onto the top of the nutrient agar slice. The growth plate was closed with the growth plate lid and the closed growth plate was placed in an incubator at 35° C. After 15 hours, 0.5 ml of an MTT solution (1 mg/ml) in phosphate buffer (pH 8.0) was added between the inner dish ring and the middle dish ring of the growth plate. The growth plate with nutrient agar and filter then was incubated for 3 more hours. After 18 hours of incubation, cell growth was counted: all of the colonies, including small and invisible ones that were not colored on the surface of filter, obtained a dark violet color and became easily visible on the white surface of the filter. The advantages observed in this investigation in comparison with conventional growth plates were that the colonies could be analyzed several hours earlier than usual, i.e., after 18 hours instead of the usual 24 hours, because even very small colonies became more visible and countable; and much smaller amounts of materials, media, and energy were needed to obtain the observed results.

Example 2

Rapid Detection of Urinary Tract Infections

Rapid detection of microorganisms in human samples often is vital for timely patient treatment. Rapid detection of micro-colonies can be done with the use of a micro-channel plate (micro-channel technology) as described in U.S. Published Patent Application No. 20050026135.

In this investigation, a micro-channel plate was attached above a filter and fixed in a special frame used for filtration of a sample. Nutrient agar (TSA, 5 mm thickness) was sliced from a container of the present invention and placed in the middle of a growth plate of the present invention. The frame containing the micro-channel plate and filter was placed in the middle of the growth plate. The frame was placed between the middle dish ring and the inner dish ring of the growth plate and nutrient agar was attached to the filter. Nutrient substances from the nutrient agar were allowed to fill all of the micro-channels of the micro-channel plate. After placing the whole device in an incubator at 37° C., microorganisms inside some of the channels actively started to grow and create micro-colonies. High cylindrical micro-colonies consisting of about 50-200 cells appeared after 6 to 7 hours of incubation. After 7 hours, the growth plate was opened and nutrient agar was removed. A pure agar slice (5 mm thickness) was cut from the container of the present invention and filled with MTT (2 mg/ml phosphate buffer pH 8.0, 1.5% of agar), transferred onto the same growth plate, and incubated for 30 minutes. The results revealed the presence of violet-colored cells in the micro-channels, which indicated that cells were present in the initial sample and could be counted.

The advantages of this method were that the results of this analysis could be obtained three times faster than normal, i.e., in 7.5 hours instead of the usual 24 hours.

Example 3

Determination of *E. Coli* in a Grape Juice Sample by Fluorescence for Quality Control Purposes In this investigation, a liquid sample, presumably containing *E. coli*, was filtered through a black nitrocellulose filter (25 mm in diameter and 0.2 µk pores; Pall Corporation). Nutrient agar (MacConkey Agar, Difco Corp.) was prepared in a storage container of the present invention, sliced (3 mm thickness), and moved to a growth plate of the present invention. The filter was mounted above the growth plate. The growth plate was closed with a growth plate lid of the present invention and the closed growth plate was incubated for 24 hours at 38° C. After incubation, 0.5 mL of a fluorogenic substrate, 4-methylumbelliferyl-β-D-glucuronide (0.1 mg/ml of 20% ethanol and 80% distilled water), was added between the inner dish ring and the middle dish ring of the growth plate. Colonies of *E. coli* obtained a bright blue fluorescence within the 20-30 minutes after the fluorogenic substrate was added. Fluorescent colonies were found on the surface of a black filter by using a UV lamp ($\lambda_{max}$=366 nm).

It is known that 4-methylumbelliferyl-β-D-glucuronide cannot be stored in nutrient media for a long time. Media containing this fluorogenic substrate is expensive and not reliable because large background interference appears during its storage. Thus, the advantages observed in this investigation were that the substrate could be added immediately after incubation, which decreased background fluorescence and increased reliability of the analysis. In addition, because the apparatus devices of the present invention allow for the use of a very small amount of nutrient agar, only a small amount of expensive fluorogenic substrate was needed.

Conclusions Based on Investigations Described in Examples 1-3

The present invention provides an apparatus comprised of devices and methods thereof which possess superior characteristics and advantages over other microorganism growth and analytic devices using solid nutrient media, such as:

(1) a very small amount of nutrient media can be used successfully without risk of dehydration, which is much more economical than conventional devices;

(2) the apparatus comprising the devices of the present invention are less expensive than those currently being used for the same purpose because they are small, require less material for manufacturing, take up less space in a laboratory, and thus more of them can be incubated in the same incubator at the same time;

(3) the apparatus comprised of the devices of the present invention can be manipulated more easily, in that the melting and filling of the storage container with nutrient agar need be done only once. In addition, the slicing of the agar is simple and cost-effective; and (4) many different kinds of indicator and growth influence substances can be used after culturing because nutrient agars are able to be exposed to such substances from the bottom and all sides of the growth plate. Typical agars in conventional plates only are accessible via the upper surface where colonies grow. This affords the opportunity to use the apparatus comprised of the devices of the present invention in numerous methods and modifications.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the claims appended and any and all equivalents thereof.

What is claimed is:

1. A growth plate, comprising:
   a growth plate lid having an exterior surface, an interior surface and a perimeter, said growth plate lid comprising an outer lid ring having an interior surface with at least one indentation therein, said outer lid ring extending substantially perpendicular from said interior surface of said growth plate lid, said outer lid ring being disposed substantially adjacent to said perimeter of said growth plate; and an inner lid ring having an interior surface and at least one slot therein, said inner lid ring extending substantially perpendicular from said interior surface of said growth plate lid; and
   a growth plate dish having an exterior surface, an interior surface and a perimeter, said growth plate dish comprising an outer dish ring having at least one slot therein, said outer dish ring extending substantially perpendicular from said interior surface of said growth plate dish; a middle dish ring having at least one slot therein, said middle dish ring extending substantially perpendicular from said interior surface of said growth plate dish; and an inner dish ring having a plurality of solid, removable segments, said solid removable segments extending substantially perpendicular from said interior surface of said growth plate dish,
   wherein said outer dish ring is positioned substantially adjacent to said interior surface of said outer lid ring, and said middle dish ring is positioned substantially adjacent to said interior surface of said inner lid ring.

2. The growth plate according to claim 1, wherein said at least one indentation in said outer lid ring is positioned at an angle from said at least one slot in said inner lid ring.

3. The growth plate according to claim 1, wherein said at least one slot in said outer dish ring is positioned at an angle from said at least one slot in said middle dish ring.

4. The growth plate according to claim 1, wherein when said growth plate is in a closed position, said at least one indentation of said outer lid ring of said growth plate overlaps with said outer dish ring of said growth plate dish because said at least one slot of said outer dish ring is not adjacent to said at least one indentation in said outer lid ring.

5. The growth plate according to claim 1, wherein when said growth plate is in an open position, said at least one indentation of said outer lid ring of said growth plate is adjacent to said at least one slot in said outer dish ring, which opens up a passage of air in said growth plate, which said passage of air can be regulated by shifting said outer lid ring in relation to said outer dish ring.

6. The growth plate according to claim 1, wherein when said at least one slot of said inner lid ring and said at least one slot of said middle dish ring are adjacent to one another, an inner passage of air is opened in the growth plate dish.

7. The growth plate according to claim 1, wherein when said at least one slot of said inner lid ring and said at least one slot of said middle dish ring are not adjacent to one another, inner space of the growth plate dish is closed to an inner passage of air.

8. The growth plate according to claim 7, wherein when said inner passage is closed to air, the at least one indentation in said outer lid ring and said at least one slot of said inner lid ring are positioned at an angle to said at least one slot of said outer dish ring and said at least one slot of said middle dish ring, said inner space of said growth plate dish being protected from contamination.

9. The growth plate according to claim 1, wherein said middle dish ring and said inner dish ring of said growth plate are substantially circular in shape and wherein said outer dish ring of said growth plate is substantially circular or rectangular in shape.

10. The growth plate according to claim 1, wherein said inner lid ring of said growth plate lid is substantially circular in shape and said outer lid ring of said growth plate lid is substantially circular or rectangular in shape.

* * * * *